United States Patent
Hayman et al.

(10) Patent No.: US 10,806,371 B2
(45) Date of Patent: Oct. 20, 2020

(54) ILLUMINATION SYSTEMS AND DEVICES FOR TRACHEAL TUBES

(71) Applicant: Covidien LP, Boulder, CO (US)

(72) Inventors: Sarah Hayman, Boulder, CO (US); Lockett E. Wood, Lyons, CO (US); Christina Goehrig, Boulder, CO (US)

(73) Assignee: Covidien LP, Mansfield, MA (US)

( * ) Notice: Subject to any disclaimer, the term of this patent is extended or adjusted under 35 U.S.C. 154(b) by 69 days.

(21) Appl. No.: 15/785,183

(22) Filed: Oct. 16, 2017

(65) Prior Publication Data
US 2018/0035912 A1    Feb. 8, 2018

Related U.S. Application Data

(63) Continuation of application No. 13/116,921, filed on May 26, 2011, now Pat. No. 9,788,755.

(51) Int. Cl.
*A61B 5/06*    (2006.01)
*A61M 16/04*    (2006.01)

(52) U.S. Cl.
CPC .............. *A61B 5/061* (2013.01); *A61M 16/04* (2013.01); *A61M 16/0404* (2014.02); *A61M 16/0443* (2014.02); *A61M 16/0459* (2014.02); *A61M 16/0484* (2014.02); *A61M 16/0486* (2014.02); *A61M 16/0488* (2013.01); *A61M 2205/3306* (2013.01); *A61M 2205/502* (2013.01); *A61M 2205/587* (2013.01)

(58) Field of Classification Search
CPC ... A61B 1/0661; A61B 1/0676; A61B 1/0684; A61B 1/267; A61B 1/2676; A61B 1/00105
See application file for complete search history.

(56) References Cited

U.S. PATENT DOCUMENTS

| | | | |
|---|---|---|---|
| 3,674,013 A * | 7/1972 | Polanyl | A61B 1/00165 600/325 |
| 4,685,457 A | 8/1987 | Donenfeld et al. | |
| 4,819,664 A * | 4/1989 | Nazari | A61M 16/04 128/207.15 |
| 4,846,153 A * | 7/1989 | Berci | A61B 1/00135 600/109 |
| 4,949,716 A | 8/1990 | Chenoweth et al. | |
| 4,982,729 A | 1/1991 | Wu et al. | |
| 5,005,573 A | 4/1991 | Buchanan | |
| 5,016,614 A | 5/1991 | MacAllister | |
| 5,038,766 A | 8/1991 | Parker et al. | |
| 5,174,283 A | 12/1992 | Parker et al. | |
| 5,203,320 A | 4/1993 | Augustine et al. | |

(Continued)

*Primary Examiner* — Timothy J Neal
*Assistant Examiner* — Jae Woo
(74) *Attorney, Agent, or Firm* — Fletcher Yoder P.C.

(57) ABSTRACT

Various embodiments of an intubation system include a tracheal tube and an illumination assembly that is removably couplable to a tubular body of the tracheal tube. The tracheal tube may be a double lumen tracheal tube having a first cuff that is adapted to be inflated to seal against the walls of a patient's trachea and a second cuff that is adapted to be inflated to seal against the walls of the patient's bronchial stem. The illumination assembly may have one or more illumination devices that are adapted to produce light within the patient's trachea, the patient's bronchial stem, or both when the illumination assembly is coupled to the tubular body.

19 Claims, 5 Drawing Sheets

(56) References Cited

U.S. PATENT DOCUMENTS

| | | | |
|---|---|---|---|
| 5,259,377 A | 11/1993 | Schroeder | |
| 5,285,778 A * | 2/1994 | Mackin | A61M 16/04 128/200.26 |
| 5,329,940 A | 7/1994 | Adair et al. | |
| 5,339,805 A | 8/1994 | Parker et al. | |
| 5,400,771 A | 3/1995 | Pirak et al. | |
| 5,607,386 A | 3/1997 | Flam et al. | |
| 5,636,625 A | 6/1997 | Miyagi et al. | |
| 5,660,175 A * | 8/1997 | Dayal | A61M 16/00 128/207.15 |
| 5,694,929 A | 12/1997 | Christopher et al. | |
| 5,921,917 A | 7/1999 | Barthel et al. | |
| 5,964,217 A | 10/1999 | Christopher et al. | |
| 6,142,144 A | 11/2000 | Pacey | |
| 6,189,000 B1 | 2/2001 | Gwertzman et al. | |
| 6,189,533 B1 | 2/2001 | Simon et al. | |
| 6,196,225 B1 | 3/2001 | Allgeyer | |
| 6,211,626 B1 | 4/2001 | Lys et al. | |
| 6,260,994 B1 * | 7/2001 | Matsumoto | G01J 3/02 362/574 |
| 6,443,156 B1 | 9/2002 | Niklason | A61M 16/04 128/207.14 |
| 6,449,006 B1 | 9/2002 | Shipp | |
| 6,459,919 B1 | 10/2002 | Lys et al. | |
| 6,520,183 B2 * | 2/2003 | Amar | A61M 16/04 128/207.14 |
| 6,543,446 B1 | 4/2003 | Christopher | |
| 6,550,475 B1 * | 4/2003 | Oldfield | A61M 16/04 128/200.26 |
| 6,568,388 B2 | 5/2003 | Christopher | |
| 6,585,639 B1 * | 7/2003 | Kotmel | A61B 1/00082 600/114 |
| 6,631,713 B1 | 10/2003 | Christopher | |
| 6,672,305 B2 | 1/2004 | Parker | |
| 6,796,939 B1 * | 9/2004 | Hirata | A61B 1/00036 600/109 |
| 6,860,264 B2 | 3/2005 | Christopher | |
| 6,929,600 B2 | 8/2005 | Hill | |
| 6,961,600 B2 | 11/2005 | Kohl et al. | |
| 6,997,918 B2 * | 2/2006 | Soltesz | A61B 17/12022 128/200.24 |
| 7,052,456 B2 | 5/2006 | Simon | |
| 7,121,280 B2 * | 10/2006 | Kyle, Jr. | A61M 16/04 128/207.14 |
| 7,297,105 B2 | 11/2007 | Mackin | |
| 7,413,543 B2 | 8/2008 | Banik et al. | |
| 7,578,786 B2 | 8/2009 | Boulais et al. | |
| 7,629,659 B2 * | 12/2009 | Jacobsen | A61B 1/05 257/432 |
| 7,670,282 B2 * | 3/2010 | Mathis | A61B 1/0014 600/101 |
| 7,787,939 B2 * | 8/2010 | Jacobsen | A61B 1/05 348/65 |
| 7,921,847 B2 * | 4/2011 | Totz | A61M 16/04 128/200.26 |
| 2002/0001202 A1 * | 1/2002 | Williams | A61B 17/02 362/572 |
| 2002/0007110 A1 * | 1/2002 | Irion | A61B 1/00181 600/170 |
| 2003/0035048 A1 | 2/2003 | Shipp | |
| 2004/0111069 A1 * | 6/2004 | Schaaf | A61M 16/0463 604/284 |
| 2005/0033285 A1 | 2/2005 | Swanson et al. | |
| 2005/0039754 A1 * | 2/2005 | Simon | A61B 1/00032 128/207.14 |
| 2005/0075538 A1 | 4/2005 | Banik et al. | |
| 2005/0119527 A1 | 6/2005 | Banik et al. | |
| 2005/0154262 A1 | 7/2005 | Banik et al. | |
| 2005/0197536 A1 | 9/2005 | Banik et al. | |
| 2005/0222499 A1 | 10/2005 | Banik et al. | |
| 2006/0004257 A1 * | 1/2006 | Gilad | A61B 1/04 600/160 |
| 2006/0025650 A1 | 2/2006 | Gavriely | |
| 2006/0173245 A1 | 8/2006 | Todd et al. | |
| 2007/0049794 A1 * | 3/2007 | Glassenberg | A61B 1/00032 600/109 |
| 2007/0106122 A1 * | 5/2007 | Yokota | A61B 1/00048 600/188 |
| 2007/0215162 A1 * | 9/2007 | Glassenberg | A61B 1/00082 128/207.15 |
| 2008/0029100 A1 * | 2/2008 | Glassenberg | A61B 1/04 128/207.15 |
| 2008/0039715 A1 | 2/2008 | Wilson et al. | |
| 2008/0086072 A1 | 4/2008 | Bonutti et al. | |
| 2009/0040754 A1 | 2/2009 | Brukilacchio et al. | |
| 2009/0143645 A1 * | 6/2009 | Matthes | A61B 1/267 600/120 |
| 2009/0149715 A1 * | 6/2009 | Mao | A61B 1/32 600/202 |
| 2010/0030020 A1 | 2/2010 | Sanders et al. | |
| 2010/0030057 A1 | 2/2010 | Gavriely et al. | |
| 2010/0076266 A1 | 3/2010 | Boulais et al. | |
| 2010/0078999 A1 | 4/2010 | Celenza et al. | |
| 2010/0113916 A1 * | 5/2010 | Kumar | A61B 5/06 600/424 |
| 2010/0326703 A1 * | 12/2010 | Gilad | A61B 1/041 174/254 |
| 2011/0196204 A1 * | 8/2011 | Setty | A61B 1/00052 600/120 |
| 2012/0004544 A9 * | 1/2012 | Saadat | A61B 1/00089 600/433 |
| 2012/0024292 A1 | 2/2012 | Sandmore et al. | |
| 2012/0172664 A1 | 7/2012 | Hayman et al. | |
| 2012/0179009 A1 | 7/2012 | Gavriely | |
| 2012/0298111 A1 | 11/2012 | Wood et al. | |
| 2014/0213850 A1 * | 7/2014 | Levy | A61B 1/00137 600/156 |
| 2014/0296643 A1 * | 10/2014 | Levy | A61B 1/00096 600/160 |

\* cited by examiner

ILLUMINATION SYSTEMS AND DEVICES FOR TRACHEAL TUBES

This application is a continuation of U.S. patent application Ser. No. 13/116,921 filed May 26, 2011, the entire contents of which are hereby incorporated by reference.

BACKGROUND

The present disclosure relates generally to medical devices and, more particularly, to tracheal tubes that may accommodate an illumination system, which may be associated with a viewing device.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the course of treating a patient, a tube or other medical device may be used to control the flow of air, food, fluids, or other substances into and out of the patient. For example, medical devices, such as tracheal tubes, may be used to control the flow of air or other gases through a trachea of a patient. Such tracheal tubes may include endotracheal tubes (ETTs), tracheostomy tubes, or transtracheal tubes. In many instances, it is desirable to provide a seal between the outside of the tube or device and the interior of the passage in which the tube or device is inserted, such as the trachea. In this way, substances can only flow through the passage via the tube or other medical device inserted in the tube, allowing a medical practitioner to maintain control over the type and amount of substances flowing into and out of the patient.

Depending on the clinical condition of the patient, a tracheal tube may be inserted that is capable of ventilating one lung or the other. For example, during thoracic surgery, surgeons may wish to isolate and perform surgery on an affected lung while simultaneously ventilating the healthy lung. Endobronchial tubes with dual lumens are typically used for this purpose. These tubes allow independent control of each lung through the separate lumens. One lumen may be blocked off to isolate the infected lung, while respiratory and anesthetic gases may be transferred through the other lumen. While endotracheal tubes involve correct tracheal placement, endobronchial tubes involve additional positioning within the correct bronchus. Such placement is often difficult and, as such, is typically mediated by bronchoscopes that are threaded through the bronchial lumen to visualize the surrounding tissue and determine whether the bronchial lumen has been correctly positioned. However, many drawbacks are associated with the use of bronchoscopes because, for example, they are bulky and difficult to operate within the relatively small diameter of the bronchial lumen. Additionally, because of the relatively high cost of bronchoscopes and the difficulty associated with cleaning these devices, a single bronchoscope may sometimes be utilized in multiple patients, thereby introducing the possibility of cross-contamination in some cases.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

As described in detail below, embodiments of an endotracheal tube (ETT) are disclosed that may accommodate an externally disposed imaging device and/or an illumination system capable of providing illumination for the external imaging device. In a particular embodiment, the tracheal tube may be an endobronchial tube. Endobronchial tubes are double-lumen tracheal tubes that facilitate an airtight seal in the trachea and one stem of a patient's bronchus to allow independent ventilation of one lung. Generally, an endobronchial tube includes two tubes of unequal length that are attached to one another. One tube terminates within the tracheal airway space, i.e., the shorter tube has a distal end at a location similar to a typical endotracheal tube. The other, longer, tube is configured to extend past the shorter tube and into a left or right bronchial stem. Both tubes define a passageway for transferring gases to and from a patient.

While the total diameter of an endobronchial tube may be larger than that of a single lumen endotracheal tube, the diameter of each individual lumen of the endobronchial tube is relatively smaller than that of a single lumen endotracheal tube. Such a shift in diameter may be challenging for physicians during placement of an endobronchial tube. Because the endobronchial tube involves not only correct intubation within the trachea but also correct placement of the bronchial lumen within a left or right bronchial stem, physicians may use visualizing devices, such as bronchoscopes, to aid in the placement of the bronchial tube. However, commercial bronchoscopes are generally sized and shaped to be used in conjunction with the relatively larger lumen of a single-lumen endotracheal tube. As such, the bronchoscopes may not fit easily within either lumen of a double-lumen endobronchial tube.

The systems and devices provided herein offer an approach to overcoming these drawbacks by enabling clinicians to couple an illumination assembly to existing endobronchial tubes to facilitate better visualization of the endobronchial tube placement. For example, in one embodiment, the illumination assembly may provide light that enhances the operation of an imaging device disposed external to the ventilation lumens of the endobronchial tube. That is, some embodiments may employ an imaging device, such as a camera mounted on a collar configured to be placed about a tubular body of the endobronchial tube, in conjunction with the disclosed illumination devices to visualize portions of a patient's airway. In particular embodiments, these features may be advantageous for use with dual-lumen endobronchial tubes during initial placement of the tubes in the patient's airway, when the patient is moved during a period of prolonged intubation, and periodically during a medical procedure.

As such, provided herein are illumination systems and devices that are removably couplable to portions of tracheal tubes and, when coupled to a tracheal tube, are operable to generate light for visualization of a portion of a patient's airway. For example, in some embodiments, the illumination systems may include one or more illumination devices, such as light emitting diodes (LEDs), mounted on a circuit board configured to be coupled to an outer portion of a tubular body of a tracheal tube. In particular embodiments, the illumination devices may be coupled to heat dissipating and/or spreading arrangements, such as metallic (e.g., copper) padding, configured to transfer heat away from the illumination devices when such devices are being operated to produce light within the patient's airway. Still further, in certain embodiments, a medical practitioner may couple the illumination system to the tracheal tube prior to insertion into the patient's airway. As such, these embodiments may include one or more features that facilitate ease of insertion of the tracheal tubes with the mounted illumination systems into the patient. For example, one embodiment includes a cuff that encases the illumination devices and is configured to be inflated to produce a volume of air between the illumination devices and a wall of the cuff.

The tracheal tubes, as provided herein, may be disposable rather than reusable, capable of conveying gas to and from the patient, and capable of providing separate ventilation channels to the tracheal space and to an individual lung. It should be noted that the provided tracheal tubes and methods of operating the tracheal tubes may be used in conjunction with auxiliary devices, such as airway accessories, ventilators, humidifiers, and so forth, which may cooperate with the tracheal tubes to maintain airflow to and from the lungs of the patient. For instance, the tracheal tubes may be placed in the trachea and coupled to a ventilator to protect the airway from possible obstruction or occlusion in emergency situations, such as when a patient experiences cardiac or respiratory arrest. For further example, the tracheal tubes may be coupled to an adapter or connector that is configured to cooperate with control circuitry to activate valving that controls the airflow to and from the patient during inspiration and expiration.

Furthermore, although the embodiments of the present disclosure illustrated and described herein are discussed in the context of endotracheal tubes such as endobronchial tubes, it should be noted that presently contemplated embodiments may include the disclosed illumination assemblies associated with any of a variety of suitable airway devices. For example, the illumination assemblies may be utilized in conjunction with a tracheostomy tube, a Broncho-Cath™ tube, a specialty tube, or any other airway device with a main ventilation lumen. Furthermore, as used herein, the term "tracheal tube" may include an endotracheal tube, a tracheostomy tube, a Broncho-Cath™ tube, a bronchoblocking tube, a specialty tube, or any other airway device. In addition, such illumination assemblies may be incorporated into catheters or other inserted or implantable medical devices that may benefit from improved illumination and/or visualization. For example, the disclosed illumination and visualization systems may be utilized with any desired catheter, such as cardiac or urinary catheters. For further example, these systems may be coupled to feeding tubes to facilitate the insertion of such tubes into a patient, for example via the esophagus into the stomach.

Figure 1:
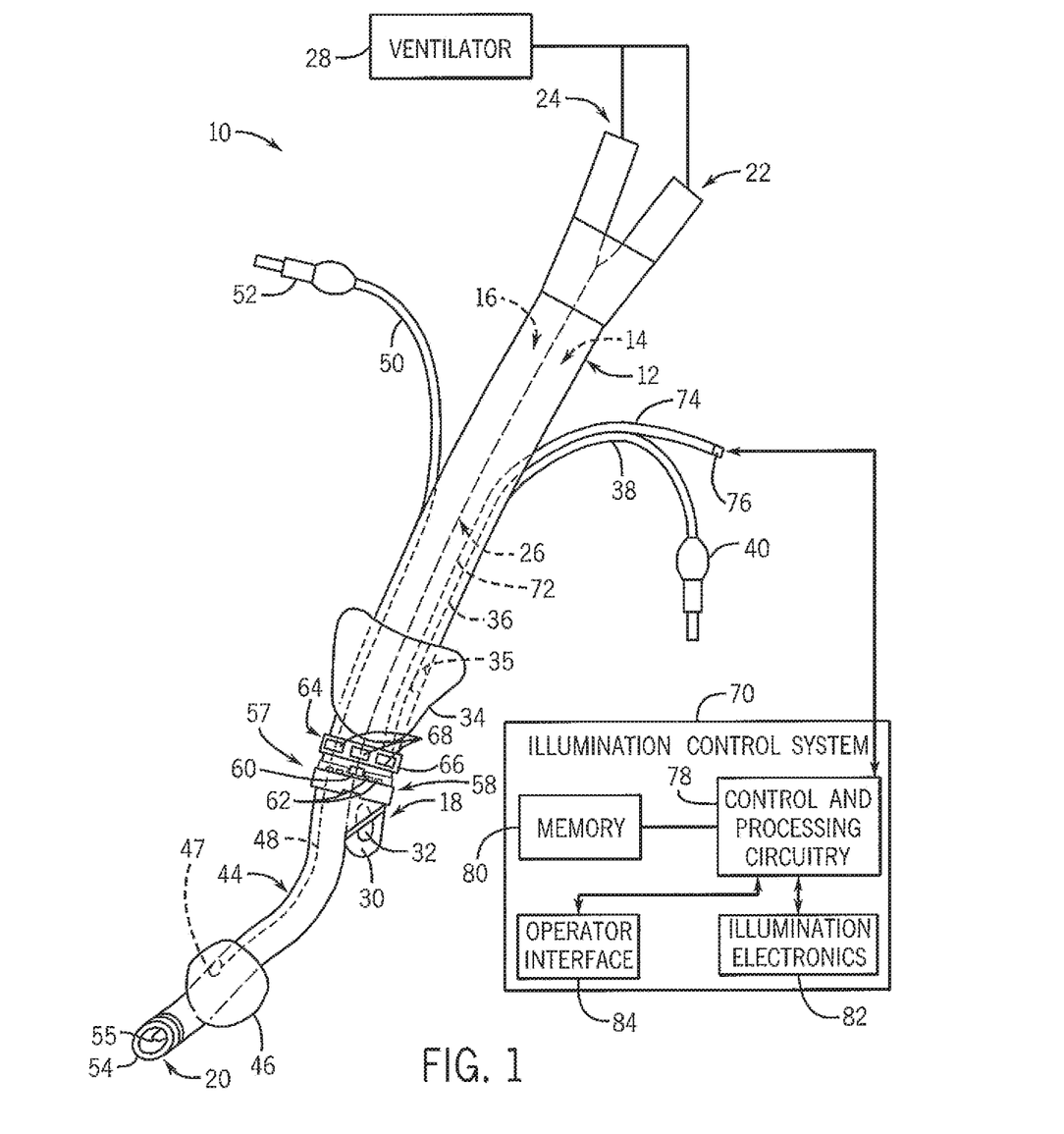
FIG. 1 is an elevational view of an endobronchial tube including an imaging device and an illumination assembly in accordance with an embodiment of the present disclosure.

Turning now to the drawings, FIG. 1 is an elevational view of an exemplary tracheal tube 10 configured to be placed in a patient's bronchial stem in accordance with aspects of the present disclosure. The tracheal tube 10 includes a central tubular body 12 with a tracheal ventilation lumen 14 and a bronchial ventilation lumen 16. The tracheal lumen terminates at a tracheal lumen distal end 18 while the bronchial lumen terminates in a bronchial lumen distal end 20. Furthermore, the tracheal tube 10 may include a tracheal lumen proximal end 22 and a bronchial lumen proximal end 24. As shown, the tracheal ventilation lumen 14 and a bronchial ventilation lumen 16 may be attached to one another over a portion of the tubular body 12 and may separate at their respective proximal ends 22 and 24 and distal ends 18 and 20.

The tracheal lumen proximal end 22 and a bronchial lumen proximal end 24 may be outfitted with separate connectors that may be attached to a ventilation device 28 during operation. The ventilation device 28 may include a suitable controller (e.g., a processor-based control system) so that a clinician may direct airflow to and from both the tracheal ventilation lumen 14 and bronchial ventilation lumen 16. In other embodiments, either the tracheal ventilation lumen 14 or the bronchial ventilation lumen 16 may be blocked or otherwise closed such that only one of the two lumens of the tracheal tube 10 is operational.

The tracheal lumen distal end 18 of ventilation lumen 14 terminates in an opening 30 and may be placed in a patient's trachea during operation to maintain airflow to and from the patient's lungs. A Murphy's eye 32 may optionally be present and may be located on the ventilation lumen 14 opposite the opening 30 to prevent airway occlusion when the tracheal tube assembly 10 is improperly placed within the patient's trachea. As illustrated, a tracheal cuff 34 may encircle the tubular body 12 and be inflated to seal against the walls of a body cavity (e.g., a trachea). The cuff 34 may be inflated via a port 35 coupled to an inflation lumen 36 terminating in an inflation tube 38 connected to an inflation pilot balloon and valve assembly 40. Additionally, it should be noted that the cuff 34 may be any suitable cuff, such as a tapered cuff, a non-tapered cuff, and so forth. The tracheal ventilation lumen 14 may also include a suction lumen (not shown) that extends from a location on the tracheal tube 10 positioned outside the body when in use to a location on the tubular body 12 that terminates in a port located proximally to cuff 34 through which secretions may be aspirated.

Bronchial ventilation lumen 16 is longer than tracheal ventilation lumen 14 and includes a distal portion 44 that extends past the tracheal lumen distal end 18. The bronchial ventilation lumen 16 may include a bronchial inflation cuff 46 that is configured to seal against the walls of a patient's bronchial stem. The cuff 46 may be inflated via a port 47 coupled to an inflation lumen 48 terminating in an inflation tube 50 connected to an inflation pilot balloon and valve assembly 52.

The tubular body 12 and the cuff 34 may be formed from materials having desirable mechanical properties (e.g., puncture resistance, pin hole resistance, tensile strength, and so forth) and desirable chemical properties (e.g., biocompatibility). Further, in one embodiment, the walls of the cuff 34 or the cuff 46 may be made of a polyurethane (e.g., Dow Pellethane® 2363-80A) having suitable mechanical and chemical properties. In other embodiments, the walls of the cuff 34 or the cuff 46 may be made of silicone or a suitable polyvinyl chloride (PVC). In certain embodiments, the cuff 34 or the cuff 46 may be generally sized and shaped as a high volume, low pressure cuff that may be designed to be inflated to pressures between approximately 15 cm $H_2O$ and 30 cm $H_2O$. Further, bronchial cuff 46 may be a different color or include other identifying markings that allow a user to differentiate between the tracheal cuff 34 and the bronchial cuff 46.

In addition, in some embodiments, to assist in proper placement of the tube 10, one or more imaging and/or illumination devices may be placed at any appropriate location along the length of the tube 10. For example, in the illustrated embodiment, an imaging assembly 57 having a collar 58 that encircles the tubular body 12 in a location below the cuff 34 is provided. As shown, the illustrated collar 58 includes a camera 60 that is provided for visualization of the patient's anatomy as the double lumen tracheal tube 10 is inserted into the patient, when the patient has been moved into an alternate position, or at any other suitable time while the patient is intubated. In the illustrated embodiment, the collar 58 also includes illumination devices 62, which provide illumination for the camera 60. However, in other embodiments, the collar 58 may not include these illumination devices 62 and may instead rely on illumination from other sources. Still further, in certain embodiments, the illumination devices 62 may not provide adequate illumination for the camera 60, and additional illumination devices may be necessary to properly visualize the patient's airway. Additionally, it should be noted that although in the illustrated embodiment, the camera 60 and the illumination devices 62 are disposed on the collar 58, in other embodiments, such devices may be located in any desirable location on the tracheal tube 10. Indeed, some or all of the illustrated components may not be present in all embodiments, and such components may not be mounted on a collar.

In the illustrated embodiment, a removably couplable illumination assembly 64 is shown in a collar configuration disposed about the outer circumference of the tubular body 12. The illumination assembly 64 includes a flexible circuit board 66 shaped as a collar and having illumination devices 68 disposed thereon. A medical practitioner may couple the illumination assembly 64 to the tubular body 12 via any desired attachment mechanism, such as with the use of a suitable adhesive (e.g. 3M biocompatible fast-curing glue). That is, the illumination assembly 64 may be coupled to the tubular body 12 prior to insertion of the tracheal tube 10 into the patient's airway.

According to certain embodiments, the illumination assembly 64 may be shaped as a collar at least partially disposed about the tracheal tube 10 so that the illumination assembly 64 generally surrounds the tubular body 12. As shown in FIG. 1, the illumination assembly 64 has a ring-like shape that can be pulled onto the tubular body 12 prior to insertion into the patient's airway. However, in other embodiments, the shape and/or style of the illumination assembly 64 may vary. For example, in particular embodiments, the illumination devices 68 may be disposed on a generally flexible material that, when flattened, can be wrapped around the tubular body 12. Still further, although the illustrated illumination assembly 64 wraps around the circumference of the tracheal tube 10, it should be noted that such assemblies are subject to considerable variations in size, shape, and other dimensions, and the shown embodiments are merely examples. For instance, in certain embodiments, the illumination assemblies may not be configured to wrap around the circumference of the tubular body 12, as depicted in more detail below.

Figure 5:
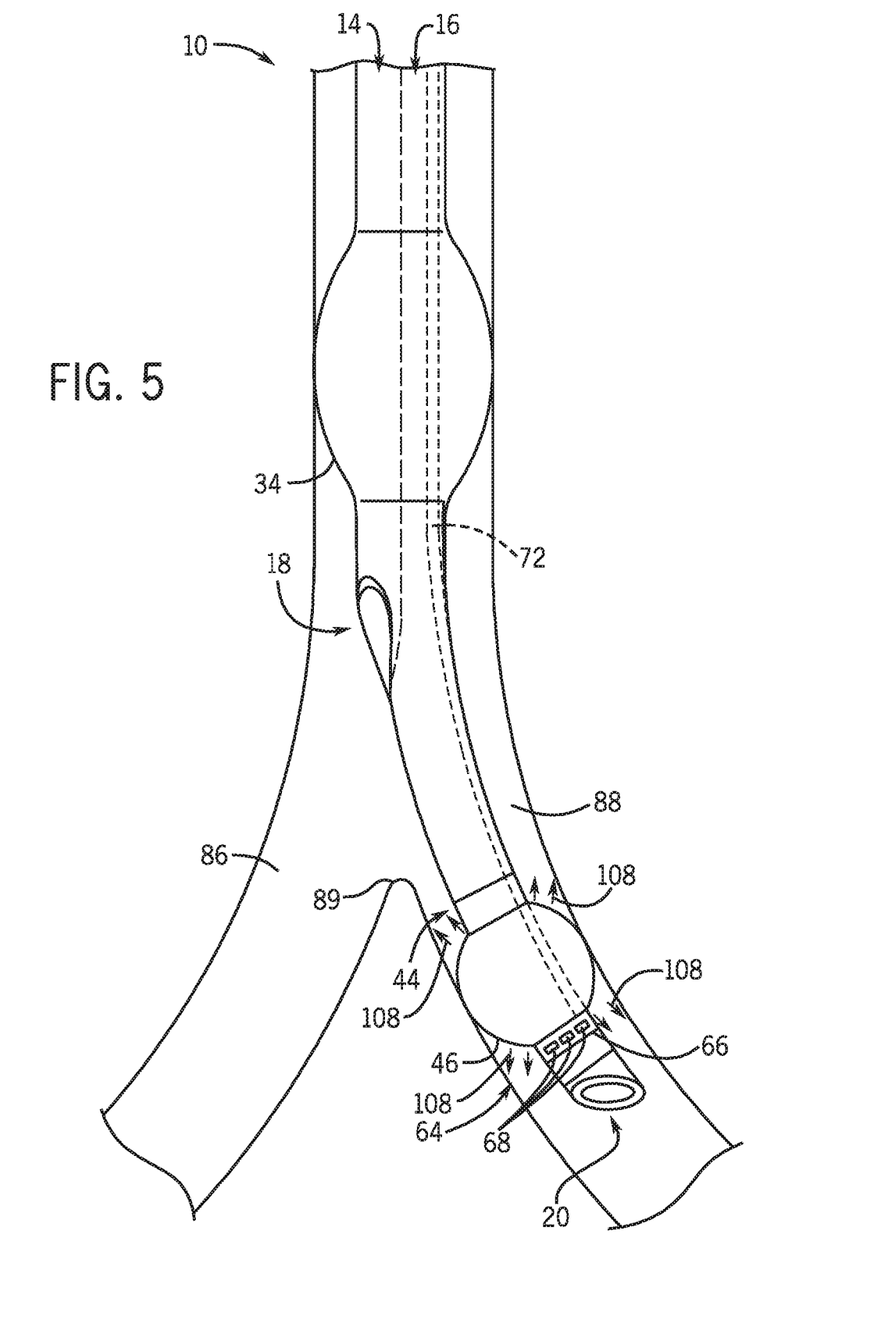
FIG. 5 is a perspective view of an embodiment of an endobronchial tube positioned within the left bronchus of a patient and having an illumination assembly disposed below a bronchial cuff of the endobronchial tube.

It should be further noted that the illumination assembly 64 may be coupled to the tubular body 12 in any suitable location along the length of the tracheal tube 10. For example, in the illustrated embodiment, the illumination assembly 66 is coupled to the tracheal tube 10 below the first cuff 34 but above the opening 30 located at the distal end 18 of the tracheal lumen 14. However, it may be advantageous to place the illumination assembly 64 in other locations, such as in a location along the distal portion 44 of the bronchial lumen 16, for example, proximal to the bronchial cuff 46, as shown in the embodiment of FIG. 5 described in detail below.

During use, the illumination devices 68 may be operated to produce light to illuminate a portion of the patient's airway. This illumination may be desirable, for example, when coordinated with operation of a visualization device, such as imaging device 60. To coordinate and/or control this operation, the illumination assembly 64 is coupled to an illumination control system 70 via a lumen 72 terminating in a tube 74 having an end connector 76. The illumination control system 70 is provided to control the activation and deactivation of the illumination devices 68 disposed on the circuit board 66. To that end, the control system 70 includes control and processing circuitry 78 associated with memory 80, illumination electronics 82, and an operator interface 84.

During operation of the illustrated airway device, the tracheal tube 10 is inserted into the trachea of a patient and positioned within the left or right bronchial stem, and the tracheal cuff 34 and bronchial cuff 46 are inflated to isolate the appropriate airway structures. The imaging assembly 57 and the illumination assembly 64 are operated to visualize the patient's anatomy, for example, during placement of the tracheal tube 10. In the illustrated embodiment, such devices are controlled by the control system 70, which is located outside the patient's body when the patient is intubated, via control wires located in the lumen 72. For example, the illumination electronics 82 located in the control system 70 provide control signals and power for the illumination devices 68. For further example, the illumination electronics 82 may exhibit control over one or more parameters (e.g., duty cycle) of the illumination devices 68 to control their functionality (and heating).

Additionally, it should be noted that although not shown in FIG. 1, the imaging assembly 57 may, via lumen 72 or another dedicated lumen, similarly be coupled to an externally located imaging control system that provides control and power for the devices mounted on the collar 58. Control and powering of one or more heat generating devices, such as those mounted on collar 58 and/or those of the illumination assembly 64, may be operated as previously disclosed in co-pending U.S. patent application Ser. No. 12/980,665, filed Dec. 29, 2010, which is hereby incorporated by reference. In these embodiments, the imaging control system may operate concurrently with the illumination control system to control operation of the imaging assembly 57 and the illumination assembly 64. Further, operation of one or both of these assemblies may be partially or fully controlled by a medical practitioner via operator interface 84. For example, the medical practitioner may choose a preset program or mode of operation on the operator interface 84, and, subsequently, the control and processing circuitry 78 may reference the memory 80 to determine how to alter one or more parameters of the devices to operate the devices in accordance with the operator's selection.

Figure 2:
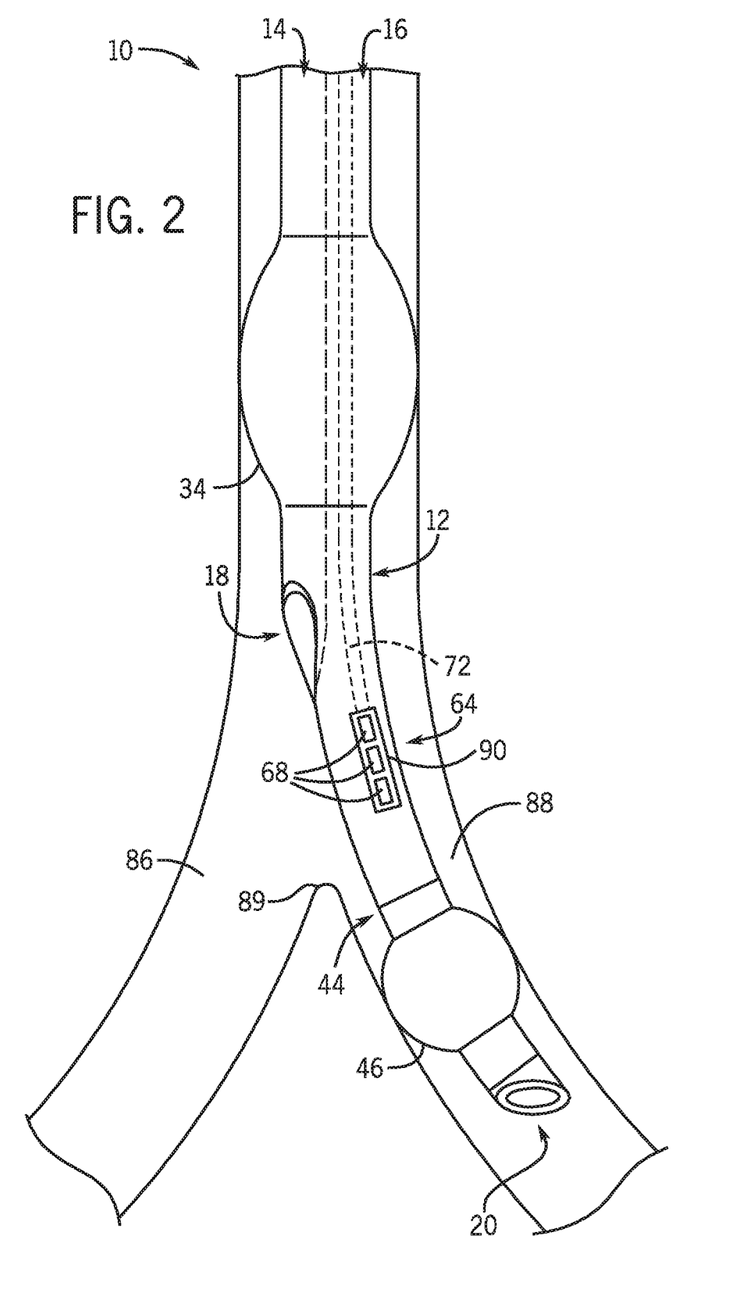
FIG. 2 is a perspective view of an embodiment of an endobronchial tube positioned within the left bronchus of a patient and having an illumination assembly disposed thereon.

Turning now to specific implementations of the illumination assemblies in accordance with certain embodiments, FIGS. 2-5 illustrate illumination assemblies independent of imaging devices. However, it is presently contemplated that these illumination assemblies could be utilized when coupled to airway devices with or without imaging devices, such as the camera of FIG. 1. Specifically, FIG. 2 is a perspective view of an embodiment of a tracheal tube 10 positioned within the left bronchus of a patient. In accordance with presently disclosed embodiments, the tube 10 may have particular features that assist in positioning the distal portion 44 and the bronchial cuff 46. For example, relative to a right bronchial stem 86, a left bronchial stem 88 is relatively curved. Accordingly, the distal portion 44 may be curved in a similar manner to help the medical practitioner position the tube 10 relative to the patient's carina 66.

Additionally, as previously mentioned, embodiments of the presently disclosed illumination assemblies, when utilized alone or in combination with an imaging device, may reduce or eliminate the need to thread a bronchoscope into the bronchial ventilation lumen 16 to visualize the tissue surrounding the bronchial distal end 20 to determine if the tube 10 has been properly positioned. In the depicted embodiment, the illumination device 64 is configured as a substantially rectangular and flexible circuit board 90 having illumination devices 68 arranged thereon. The rectangular circuit board 90 is positioned lengthwise along the tubular body 12 between the tracheal cuff 34 and the bronchial cuff 46. As such, during operation, the illumination devices 68 may be activated to produce light to illuminate the area of the patient's airway that is proximate to the distal end 18 of the tracheal lumen 16. However, in other embodiments, the depicted illumination assembly 64 may be placed in any desired location lengthwise along the tubular body 12.

Figure 3:
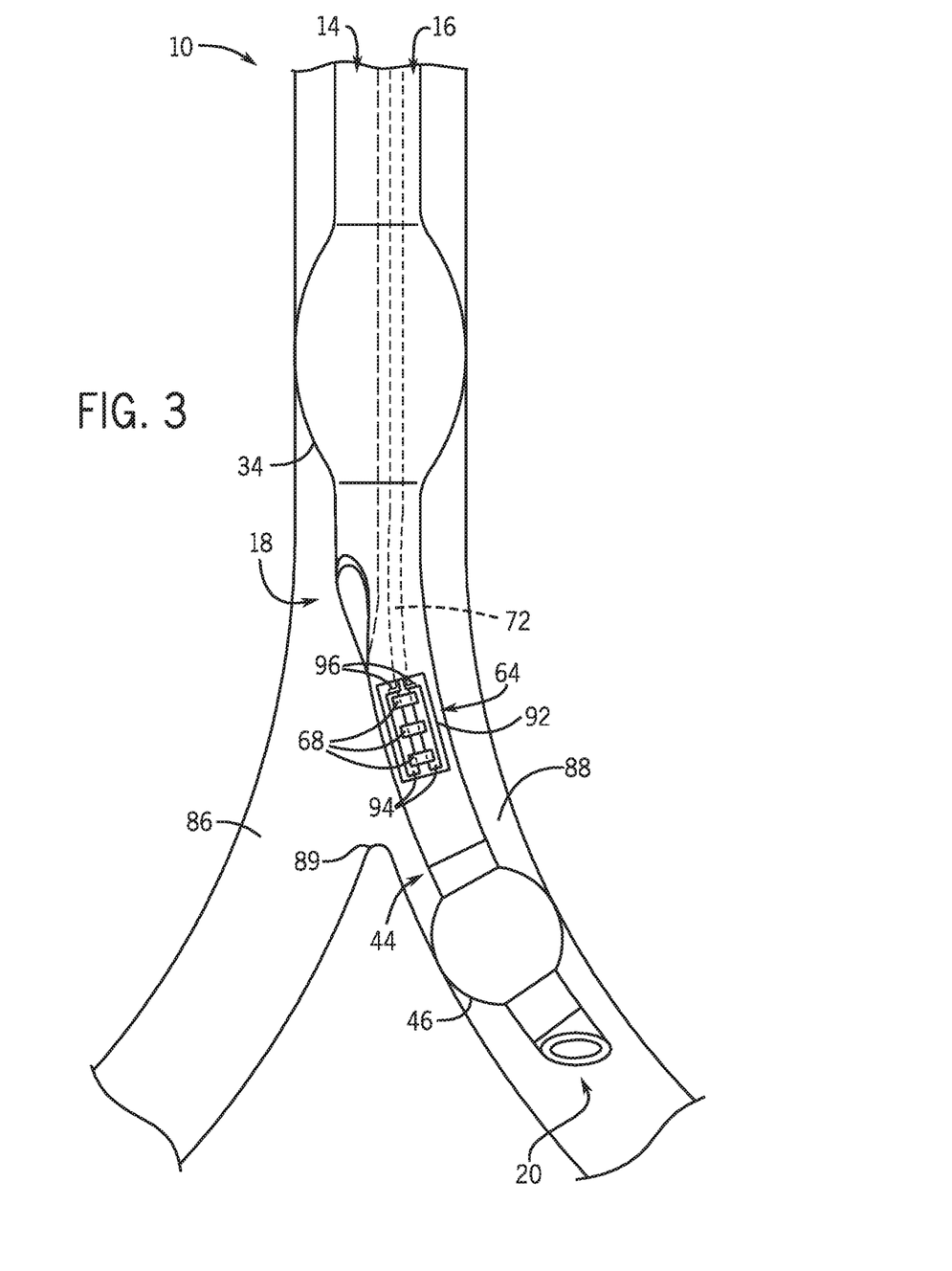
FIG. 3 is a perspective view of an embodiment of an endobronchial tube positioned within the left bronchus of a patient and having an illumination assembly with copper padding disposed thereon.

FIG. 3 illustrates a further embodiment of the illumination assembly 64 of FIG. 2. In this embodiment, the illumination assembly 64 is configured as a substantially rectangular circuit board 92 having illumination devices 68 coupled to heat dissipating and/or spreading structures, such as metallic pads 94 in the illustrated embodiment. The metallic pads 94 are coupled to cables 96 that are routed through lumen 72 to couple the circuit board 92 to an externally located illumination control system. During operation, the metallic pads 94 enable heat transfer away from the illumination devices 68 and provide an electrical power contact point. To that end, the metallic pads 94 may be made of a variety of suitable metallic materials, such as copper. Further, although the metallic pads 94 in the illustrated embodiment are rectangular to conform to the shape of the circuit board 92, in other embodiments, the pads 94 may be dimensioned according to the size and shape of the circuit board. For example, in embodiments in which the illumination devices 68 are mounted on a ring shaped structure, the metallic pads may be shaped to follow the circumference of the ring or collar. As such, the presently disclosed metallic pads may be susceptible to various modifications that enable their use with other embodiments; the application of the metallic pads is not limited to the rectangular circuit board embodiment shown in FIG. 3.

It should also be noted that the pads serve at least two roles, including the dissipation of heat generated by power applied for illumination, and spreading of such heat (to reduce temperatures of any particular locations). In performing the latter function, the pads may be considered as heat spreaders insomuch as they may render the temperatures on and near the illuminating devices more isothermal. It should also be noted that various materials, both metallic and non-metallic may be suitable for such purposes, and the structures may be made in various shapes and thicknesses depending upon their location and that of the heat sources.

Figure 4:
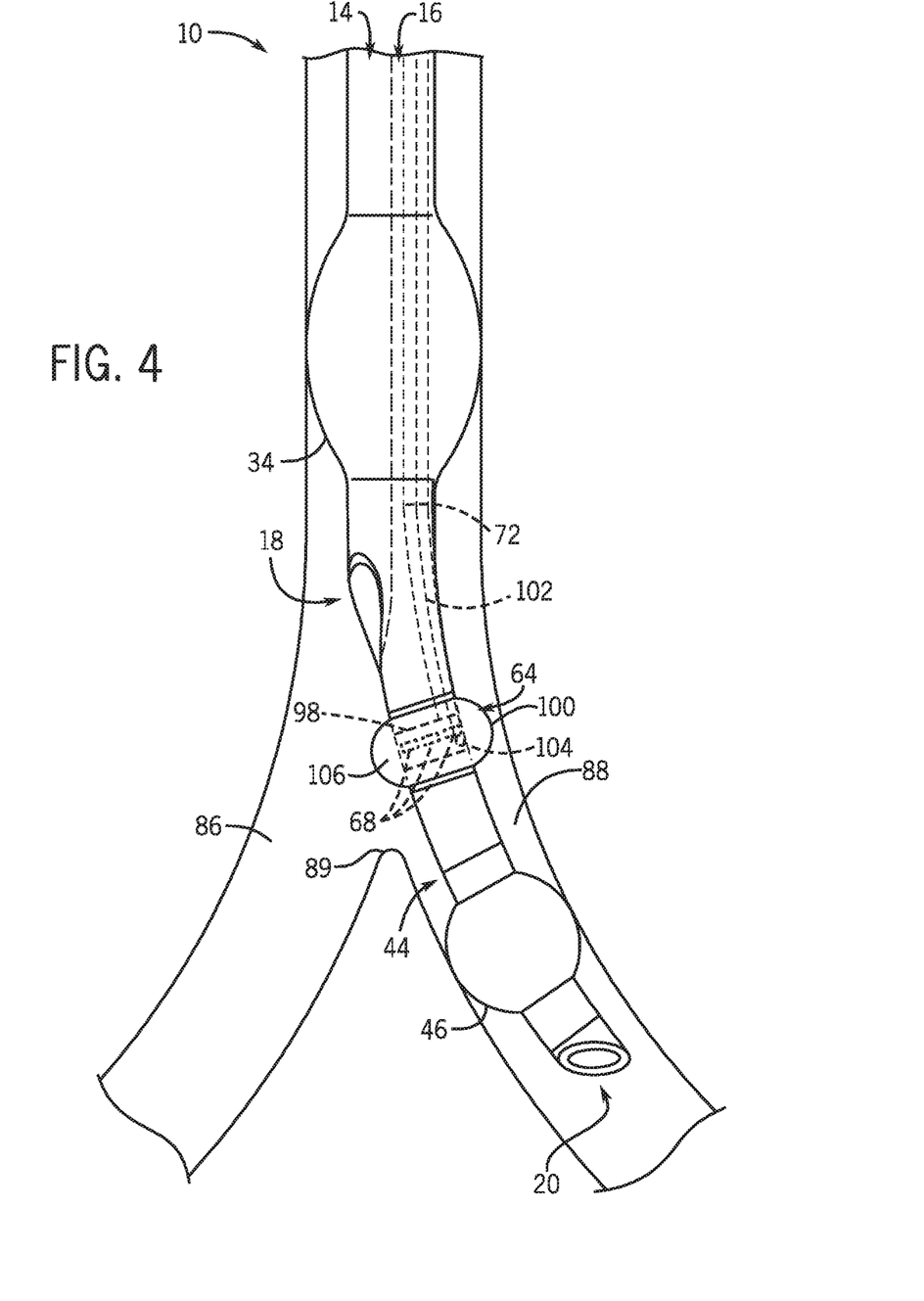
FIG. 4 is a perspective view of an embodiment of an endobronchial tube positioned within the left bronchus of a patient and having an illumination assembly with a cuff disposed about the illumination assembly and the endobronchial tube.

FIG. 4 illustrates an alternate embodiment of the illumination assembly 64 in which the illumination devices 68 are mounted on a ring-shaped circuit board 98 and encased by a cuff 100. As before, the circuit board 98 is coupled to an external control system via lumen 72. An additional inflation lumen 102 is also provided in the illustrated embodiment to enable the cuff 100 to be inflated via notch 104. However, in some embodiments, the cuff 100 may be inflated prior to placement around the tracheal tube 10, and the inflation lumen 102 may be eliminated.

During operation, the cuff 100 may be inflated prior to insertion of the tracheal tube 10 into the patient's airway. As such, a volume 106 of fluid (e.g., air) may be established between the illumination devices 68 and a wall of the cuff 100, thus providing a buffer region between the illumination devices 68 and the walls of the patient's airway. However, unlike cuffs 34 and 46, which are inflated to seal against walls of the patient's airway, cuff 100 is configured to be inflated to provide volume 106 without sufficient expansion to seal against the airway walls. Still further, in particular embodiments, the cuff 100 may be made of any suitable material that is substantially transparent enough to enable the light from illumination devices 68 to travel therethrough. For instance, the cuff 100 may be made of any of a variety of suitable plastics.

As previously noted above, embodiments of the illumination assemblies 64 disclosed herein may be disposed in a variety of locations along the length of the tubular body 12. An example of one suitable location is shown in the embodiment of FIG. 5, in which the collar 66 having illumination devices 68 is coupled to the distal portion 44 of bronchial ventilation lumen 16 below the bronchial cuff 46. In certain embodiments, the illumination assembly 64 may be coupled to the tubular body 12 adjacent to the bronchial cuff 46 or may be directly coupled to a portion of the bronchial cuff 46. In these embodiments, the illumination assembly 64 may be operated to produce light to illuminate the bronchial cuff 46, thus resulting in the bronchial cuff 46 radiating light, as shown by arrows 108. This feature may be advantageous during the placement or repositioning of the tracheal tube 10 since the illumination of the bronchial cuff 46 may facilitate proper placement of the distal portion 20 of the bronchial lumen 16 in the desired bronchial stem of the patient. As such, presently disclosed embodiments may provide a visual guide for the medical practitioner when positioning the tracheal tube 10 in the patient's airway.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed.

Rather, the various embodiments may cover all modifications, equivalents, and alternatives falling within the spirit and scope of the disclosure as defined by the following appended claims.

What is claimed is:

1. An illumination system, comprising:
   a tubular body comprising a proximal end, a distal end, and a wall extending between the proximal end and the distal end, wherein the tubular body is configured to be inserted into a bronchial ventilation lumen;
   an illumination assembly, wherein the illumination assembly comprises one or more illumination devices configured to illuminate a patient's airway, the illumination devices being disposed on a flexible circuit board coupled to an outer wall of the tubular body; and
   an imaging device positioned distal to the illumination assembly, wherein the imaging device is configured to generate an image of the patient's airway.

2. The illumination system of claim 1, wherein the flexible circuit board is positioned about a circumference of the tubular body.

3. The illumination system of claim 1, wherein the flexible circuit board is positioned lengthwise along a length of the tubular body.

4. The illumination system of claim 1, wherein the illumination assembly comprises one or more heat dissipating and/or spreading pads configured to transfer heat from the one or more illuminating devices.

5. The illumination system of claim 1, wherein the imaging device is disposed adjacent to the illumination assembly.

6. The illumination system of claim 1, wherein the one or more illuminating devices comprises a light emitting diode (LED).

7. The illumination system of claim 1, comprising an illumination control system coupled to the illumination assembly and configured to control generation of light from the illumination assembly.

8. The illumination system of claim 1, wherein the tubular body comprises a lumen formed within the wall and extending along a length of the tubular body, and wherein the lumen terminates adjacent to the illumination assembly.

9. The illumination system of claim 8, comprising a data cable and a power cable disposed within the lumen and configured to provide data and power, respectively, to the illumination assembly.

10. A system, comprising:
    an illumination assembly coupled to an outer wall of an endotracheal tube and comprising:
    a flexible circuit board thermally coupled via a heat transfer layer to the outer wall defining a tubular body configured to be inserted into a patient's airway, wherein the flexible circuit board is positioned adjacent to an opening of the tubular body; and
    one or more illumination devices disposed on the flexible circuit board and configured to illuminate the patient's airway; and
    an imaging assembly positioned distal to the illumination assembly and
    between the illumination assembly and the opening of the tubular body
    and comprising a camera configured to generate an image of the patient's airway.

11. The system of claim 10, wherein the flexible circuit board is positioned about a circumference of an outer surface of the wall.

12. The system of claim 10, wherein the flexible circuit board is positioned lengthwise along a length of the tubular body.

13. The system of claim 10, one or more heat dissipating and/or spreading pads coupled to the flexible circuit and configured to transfer heat from the one or more illuminating devices.

14. The system of claim 10, wherein the one or more illuminating devices comprises a light emitting diode (LED).

15. The system of claim 10, wherein the illumination assembly is coupled to the outer wall.

16. A system, comprising:
    an endotracheal tube configured to be inserted into a patient's airway and comprising a tubular body;
    an illumination assembly coupled to the tubular body, wherein the illumination assembly comprises a flexible circuit board coupled to a wall of the tubular body and one or more illumination devices configured to illuminate a patient's airway
    and wherein the flexible circuit board is positioned about a circumference of the tubular body, wherein the one or more illumination devices is disposed on the flexible circuit board; and
    an imaging assembly positioned adjacent the illumination assembly, wherein the imaging assembly is coupled to the wall of the tubular body and comprises a camera, wherein the imaging assembly is configured to generate an image of the patient's airway.

17. The system of claim 16, wherein the illumination assembly is positioned about a circumference of an outer surface of the wall.

18. The system of claim 16, wherein the illumination assembly is positioned at a distal end of the tubular body.

19. The system of claim 16, wherein the imaging assembly is positioned between the illumination assembly and an opening of the tubular body.

* * * * *